(12) United States Patent
Alexander et al.

(10) Patent No.: US 9,470,627 B2
(45) Date of Patent: Oct. 18, 2016

(54) DETECTION OF PARTICLE CHARACTERISTICS (71) Applicant: Xtralis Technologies Ltd, Nassau, NP (BS)

(72) Inventors: Brian Alexander, Wantirna (AU); Nitin Vayeda, Glen Waverley (AU); Kemal Ajay, Mount Waverley (AU)

(73) Assignee: Xtralis Technologies Ltd, Nassau (BS)

( * ) Notice: Subject to any disclaimer, the term of this patent is extended or adjusted under 35 U.S.C. 154(b) by 0 days.

(21) Appl. No.: 14/833,785

(22) Filed: Aug. 24, 2015

(65) Prior Publication Data

US 2016/0033400 A1 Feb. 4, 2016

Related U.S. Application Data (62) Division of application No. 13/062,301, filed as application No. PCT/AU2009/001162 on Sep. 4, 2009, now Pat. No. 9,128,047.

(30) Foreign Application Priority Data

Sep. 5, 2008 (AU) .................. 2008904626

(51) Int. Cl.
*G01N 15/02* (2006.01)
*G01N 21/53* (2006.01)
(Continued)

(52) U.S. Cl.
CPC ............. *G01N 21/53* (2013.01); *G01F 1/667* (2013.01); *G01N 15/06* (2013.01); *G01N 15/1434* (2013.01); *G08B 17/10* (2013.01);
(Continued)

(58) Field of Classification Search
CPC ............ G08B 17/107; G01N 21/53; G01N 15/1456; G01N 2015/0046; G01N 2021/4733; G01N 21/3151; G01N 21/256; G01N 21/274
USPC .......... 356/335–343, 432–440; 250/573–575
See application file for complete search history.

(56) References Cited

U.S. PATENT DOCUMENTS 4,242,673 A 12/1980 Cooper
4,573,796 A * 3/1986 Martin ............... G01N 15/1429
250/461.2

(Continued)

FOREIGN PATENT DOCUMENTS

WO WO-99/37383 A1 7/1999
WO WO-01/59737 A1 8/2001
(Continued)

OTHER PUBLICATIONS

"U.S. Appl. No. 13/062,301, Final Office Action mailed Mar. 18, 2014", 10 pgs.
(Continued)

*Primary Examiner* — Hoa Pham
(74) *Attorney, Agent, or Firm* — Schwegman Lundberg & Woessner, P.A.

(57) ABSTRACT

A method of detecting particles in an air flow is described. The method includes receiving a signal indicative of light intensity scattered from the air flow at a plurality of wavelengths and processing the signal indicative of the intensity of received light at each of the wavelengths and a corresponding wavelength dependent parameter to generate an output signal indicative of at least one characteristic of particles in the air flow. A particle detection system is also described.

7 Claims, 10 Drawing Sheets

(51) Int. Cl.
  *G08B 17/10* (2006.01)
  *G08B 17/107* (2006.01)
  *G08B 29/26* (2006.01)
  *G01F 1/66* (2006.01)
  *G01N 15/06* (2006.01)
  *G01N 15/14* (2006.01)
  *G01N 21/47* (2006.01)

(52) U.S. Cl.
  CPC ........... *G08B 17/107* (2013.01); *G08B 29/26* (2013.01); *G01N 2015/0693* (2013.01); *G01N 2021/4733* (2013.01); *G01N 2201/061* (2013.01); *G01N 2201/062* (2013.01)

(56) References Cited

U.S. PATENT DOCUMENTS

| | | | |
|---|---|---|---|
| 5,008,559 A | 4/1991 | Beyersdorf | |
| 5,239,185 A | 8/1993 | Ito et al. | |
| 5,523,743 A * | 6/1996 | Rattman | G08B 29/24 250/205 |
| 6,011,478 A | 1/2000 | Suzuki et al. | |
| 6,055,052 A | 4/2000 | Lilienfeld | |
| 7,239,387 B2 | 7/2007 | Politze et al. | |
| 7,242,009 B1 | 7/2007 | Wilson et al. | |
| 7,508,313 B2 | 3/2009 | Cole et al. | |
| 7,893,960 B1 * | 2/2011 | Wallach | G08B 13/10 348/143 |
| 8,269,639 B2 | 9/2012 | Cole et al. | |
| 8,797,531 B2 * | 8/2014 | Knox | G01N 21/53 356/337 |
| 9,057,485 B2 * | 6/2015 | Knox | G01N 21/53 |
| 9,128,047 B2 | 9/2015 | Alexander et al. | |
| 2009/0257057 A1 | 10/2009 | Novotny et al. | |
| 2011/0255087 A1 | 10/2011 | Alexander et al. | |

FOREIGN PATENT DOCUMENTS

| | | |
|---|---|---|
| WO | WO-2004/102499 A1 | 11/2004 |
| WO | WO-2005/001436 A1 | 1/2005 |

OTHER PUBLICATIONS

"U.S. Appl. No. 13/062,301, Non Final Office Action mailed Aug. 9, 2013", 11 pgs.

"U.S. Appl. No. 13/062,301, Non Final Office Action mailed Oct. 1, 2014", 11 pgs.

"U.S. Appl. No. 13/062,301, Notice of Allowance mailed Apr. 30, 2015", 8 pgs.

"U.S. Appl. No. 13/062,301, Response filed Jan. 24, 2014 to Non Final Office Action mailed Aug. 9, 2013", 16 pgs.

"U.S. Appl. No. 13/062,301, Response filed Apr. 1, 2015 to Non Final Office Action mailed Oct. 1, 2014", 13 pgs.

"U.S. Appl. No. 13/062,301, Response filed Sep. 7, 2014 to Final Office Action mailed Mar. 18, 2014", 11 pgs.

"U.S. Appl. No. 13/062,301, Response to Restriction Requirement mailed May 15, 2013", 12 pgs.

"U.S. Appl. No. 13/062,301, Restriction Requirement mailed May 15, 2013", 8 pgs.

"Chinese Application No. 200980144262.2, Office Action issued Sep. 24, 2012", 8 pgs.

"International Application No. PCT/AU2009/001162, International Search Report and Written Opinion mailed Nov. 6, 2009", 13 pgs.

* cited by examiner

FIGURE 9A Scattering vs Wavelegth - average of gradient to IR to measure smoke

FIGURE 9B Scattering vs Wavelegth - average of gradient to measure smoke

FIGURE 9C Scattering vs Wavelegth -
use gradient of best fit line to measure smoke

FIGURE 10

DETECTION OF PARTICLE CHARACTERISTICS

PRIORITY CLAIM TO RELATED APPLICATIONS

This application is a divisional application and claims the benefit of priority of U.S. patent application Ser. No. 13/062,301, filed on Mar. 4, 2011 (371(c) date of Jun. 23, 2011), which is a national stage application under 35 U.S.C. §371 of PCT/AU2009/001162, filed Sep. 4, 2009, and published as WO 2010/025520 A1 on Mar. 11, 2010, which claims priority to Australian Application No. 2008904626, filed Sep. 5, 2008, which applications and publication are incorporated herein by reference and made a part hereof in their entirety, and the benefit of priority of each of which is claimed herein.

FIELD OF THE INVENTION

The present invention relates to optical particle detection.

In a one form, the present invention relates to an optical smoke detector which uses a plurality of wavelengths of electromagnetic radiation to enable particle detection at a range of sizes. In the preferred form the invention will be described in the context of performing smoke detection using four wavelengths of light, however the invention should not be considered to be limited to this exemplary application or implementation.

BACKGROUND OF THE INVENTION

Various methods of detecting particles in air are known. One method involves projecting a beam of light across a detection chamber in which an air sample is contained and measuring the amount of light scattered at a particular scattering angle from the beam. Such particle detectors can be aspirating, in that they actively draw air into them, or alternatively they may rely on natural air currents to move air into the detection chamber.

It is known that the angular scattering properties of particles are dependent on the wavelength of incident light relative to the particle size. Accordingly, smoke and particle detectors have been made using multiple scattering angles and/or multiple wavelengths to detect particles of a predetermined size of interest. For example, UV light is scattered relatively strongly by small particles, such as smoke, but infrared light is scattered less by such particles. On the other hand UV and IR light will be equally sensitive to variations in received light intensity that are caused by factors such as drift in the system, soiling of the optics of the system or the introduction of large particles such as dust into the detection chamber.

With such multiple wavelength or scattering angle particle detection systems there is a need to be able to accurately determine whether the received signals at the multiple scattering angles or wavelengths are caused by particles of interest or nuisance particles such as dust. It is also possible to use this wavelength sensitivity or angular sensitivity of light scattering to track the nature of group of particles over time, e.g. to track the development of a fire as the smoke particle size distribution changes.

Accordingly, it is an object of an aspect of the present invention to provide means for determining whether particles of interest have entered a detection chamber using more than one wavelength of electromagnetic radiation.

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

SUMMARY OF THE INVENTION

In one aspect of the invention there is provided a method of detecting particles in an air flow including receiving a signal indicative of light intensity scattered from the air flow at a plurality of wavelengths; processing the signal indicative of the intensity of received light at each of the wavelengths and a corresponding wavelength dependent parameter to generate an output signal indicative of at least one characteristic of particles in the air flow.

The step of processing can include fitting at least one function to the signals indicative of the intensity of received light and their corresponding wavelength dependent parameters; and determining an output signal indicative of at least one characteristic of particles in the air flow on the basis of the at least one function fitted to the plurality of plotted values. Advantageously the function can be used to characterise the nature of the particles in the airflow in a manner to be described below.

A plurality of functions or a single function can be fitted to the signals indicative of the intensity of received light and their corresponding wavelength dependent parameters.

The function(s) can be, for example, a polynomial.

In some examples the output signal can be determined on the basis of a gradient at, at least one point on at least one of said functions. A plurality of linear functions could be fitted to two or more signals and their corresponding wavelength dependent parameters. In this case the output signal can be determined on the basis of the gradient of a plurality of said linear functions e.g. by averaging the gradients.

The two or more signals used to fit each linear function can represent scattered light at adjacent wavelengths. Alternatively the two or more signals used to fit each linear function can include a signal corresponding to a common wavelength.

In an alternative embodiment, the step of processing the signal indicative of the intensity of received light at each of the wavelengths and a corresponding wavelength dependent parameter includes, applying a statistical method to the signal indicative of the intensity of received light at each of the wavelengths and a corresponding wavelength dependent parameter to generate an output signal indicative of a characteristic of particles in the air flow.

In these methods the wavelength dependent parameter could be wavelength, energy or frequency; or a parameter based on wavelength, energy or frequency; or some other parameter.

In some embodiments the methods can include comparing the at least one function to one or more predetermined signatures corresponding to one or more characteristics of particles in the airflow.

The step of processing the signal indicative of the intensity of received light at each of the wavelengths and a corresponding wavelength dependent parameter to generate an output signal indicative of a characteristic of particles in the air sample can include comparing the signal indicative of the intensity of received light at a plurality of wavelengths to one or more predetermined signatures corresponding to one or more characteristics of particles in the airflow.

The comparison is preferably performed at, at least three wavelengths. In an exemplary embodiment the comparison is performed at four wavelengths.

The one or more of the predetermined signatures can relate to characteristics of particles in the airflow, including, but not limited to, particle concentration, particle size, particle size distribution, particle colour, particle composition, particle type, particle shape, fire type, fire progression stage, the type of combustion material producing the particles.

By way of example, a signature could correspond to the following particle types smoke particles, dust particles, lint particles, other nuisance particles, macroscopic foreign bodies, particles in a predetermined size range.

The method could include normalising either or both of the signals indicative of the intensity of received light or their corresponding wavelength dependent parameters, e.g. the values could be normalised with respect to the highest or lowest value.

The method can further include repeating said method one or more times to track at least one characteristic of the particles in the air sample characterised by the output signal output over time.

The method could include comparing at least one tracked characteristic over time to a time based signature. This allows certain events or conditions that have a particular temporal characteristic to be identified. With this in mind the method can include identifying a condition based on said comparison. Suitable conditions or events to identify can include, but are not limited to: a fire, a change in a fire, e.g. an increase in size, change of fuel or combustion conditions, progression of a fire stage, e.g. smouldering to flaming, a type of fire e.g. the type of combustion material, cigarette smoke or an electrical fire etc., dust producing event, e.g. an event that creates or stirs up dust, a transient nuisance condition e.g. a dust event, a detector fault e.g. failure of a light source or photo detector, encroachment of a foreign body into the detection chamber, e.g. an insect or piece of lint entering the detection chamber.

The methods can include pre-processing the signal indicative of the intensity of received light at a wavelength to remove the effect of background light.

The method can include determining a concentration of particles in a size range on the basis of the output signal.

In another aspect the present invention provides a particle detection system including, a detection chamber adapted to receive an air sample, means for illuminating the air sample at a plurality of wavelengths, means for receiving light scattered from the air sample at the plurality of wavelengths and to output a signal indicative of the intensity of received light at each of the wavelengths, processing means for processing the signal indicative of the intensity of received light at each of the wavelengths and a corresponding wavelength dependent parameter to generate an output signal indicative of at least one characteristic of particles in the air sample using a method as herein described.

In a further aspect there is provided a particle detection system including, a detection chamber adapted to receive an air sample, first particle detection means including a first light source for illuminating a first volume of the air sample at at least a first wavelength, and a first light receiver having a field of view intersecting with the first volume for receiving light scattered from the detection chamber and outputting a first signal indicative of the scattered received light; second particle detection means including a second light source for illuminating a second volume of the air sample at at least a second wavelength, and a second light receiver having a field of view intersecting with the second volume for receiving light scattered from the detection chamber and outputting a second signal indicative of the scattered received light; light source activation means adapted to selectively activate the first light source in a first time period and the second light source in a second time period; processing means adapted to receive a first signal from the first light receiver and a second signal from the second light receiver corresponding to the first time period and process the received signals to generate a first output corresponding to the first time period corrected for background light; and to receive a first signal from the first light receiver and a second signal from the second light receiver corresponding to the second time period and process the received signals to generate a second output corresponding to the second time period that is corrected for background light.

Preferably the detection chamber includes at least one wall within the field of view of each of the first and second light receivers and wherein the first and second light receivers are positioned such that substantially the same portion of said chamber wall lies within the field of view of each of the first and second light receivers.

The first and second light receivers are preferably positioned with respect to their corresponding first and second light sources such that the field of view of the first light receiver and the second volume do not intersect, and the field of view of the second light receiver and the first volume do not intersect.

The first and second wavelengths are preferably different wavelengths, but could be the same wavelength. This principle could also be extended to additional light sources and light receivers.

The first output corresponding to the first time period is preferably corrected for background light by a process including subtracting the second signal indicative of the scattered received light corresponding to the first time period from the first signal indicative of the scattered received light corresponding to the first time period.

Similarly the second output corresponding to the second time period is preferably corrected for background light by a process including subtracting the first signal indicative of the scattered received light corresponding to the second time period from the second signal indicative of the scattered received light corresponding to the second time period.

As used herein, except where the context requires otherwise, the term "comprise" and variations of the term, such as "comprising", "comprises" and "comprised", are not intended to exclude further additives, components, integers or steps.

BRIEF DESCRIPTION OF THE DRAWINGS

Preferred embodiments of the present invention will now be described by way of non-limiting example only with reference to the accompanying drawings. In the figures.

DETAILED DESCRIPTION OF THE EMBODIMENTS

Figure 1:
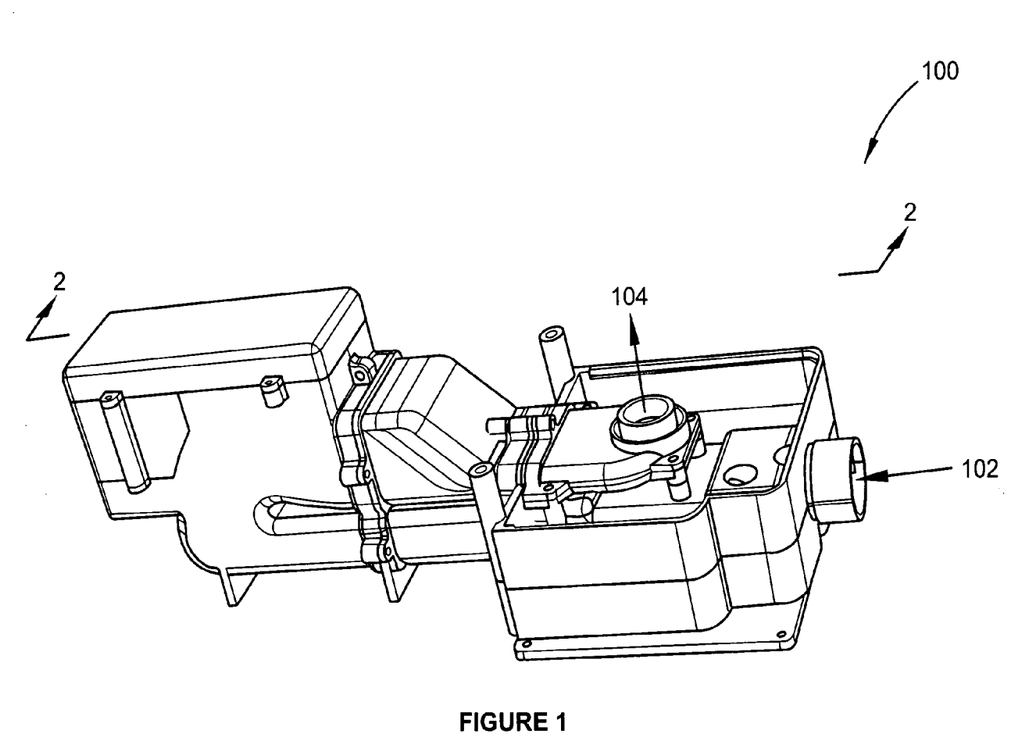
FIG. 1 illustrates a perspective view of a particle detection chamber made in accordance with an embodiment of the present invention.

FIG. 1 shows a perspective view of a detection chamber 100 of a smoke detector. The detection chamber 100 is adapted to receive an air sample drawn into it by an aspirating system (not shown) and to detect the presence of particles in the airflow. If one or more alarm conditions are met a particle detection alarm may be sounded. In the detection chamber of FIG. 1 an air sample is drawn into inlet port 102 and passes through an airflow-path through the detection chamber and is an exhausted from the detection chamber 100 via exhaust port 104. Part of the exhaust airflow may be filtered to provide a clean stream for use in cleaning the optical surfaces of the detector that are prone to particulate build-up.

Figure 2:
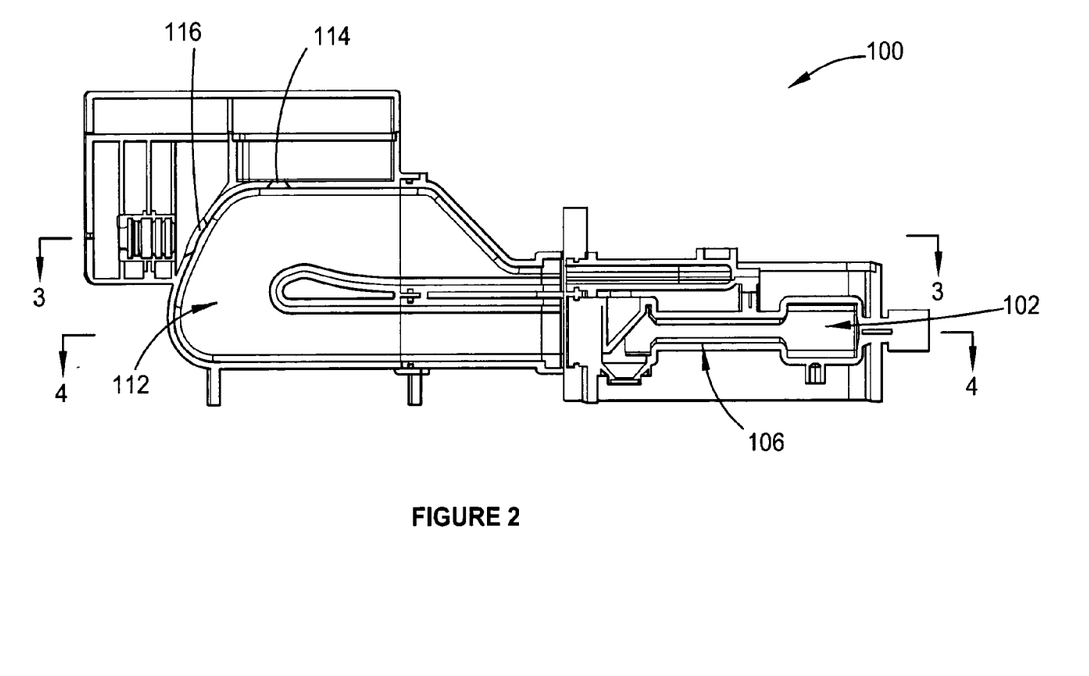
FIG. 2 shows a cross-sectional view of the detection chamber of FIG. 1 along line 2-2.
Figure 3:
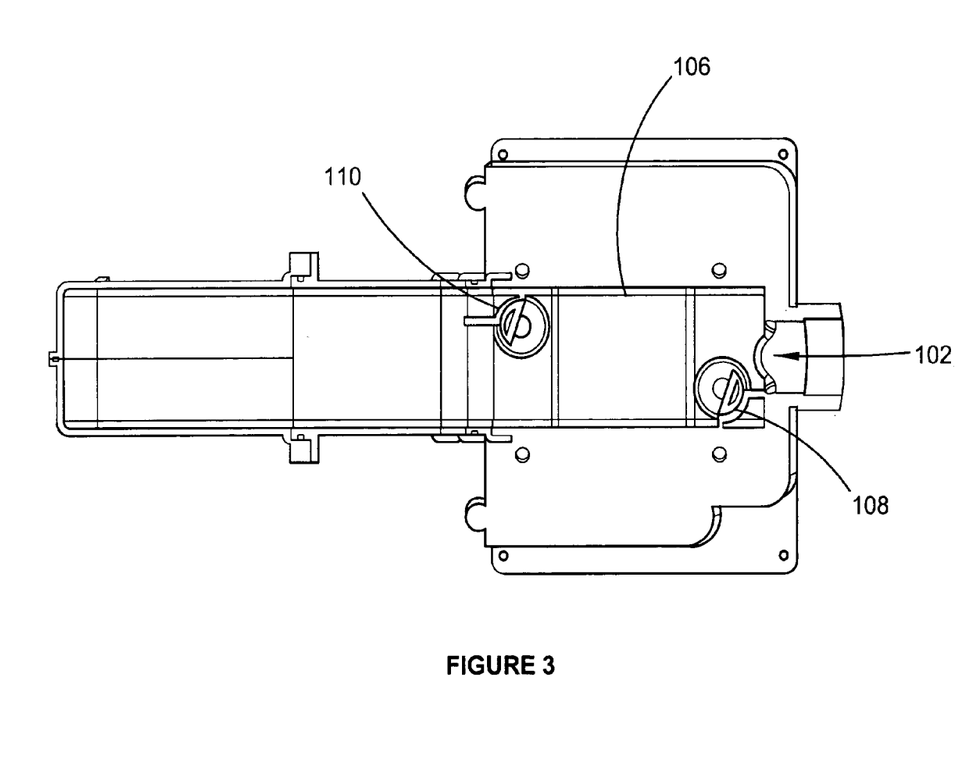
FIG. 3 illustrates a cross-sectional view of the lower part of the airflow-path through the detection chamber along line 4-4.
Figure 4:
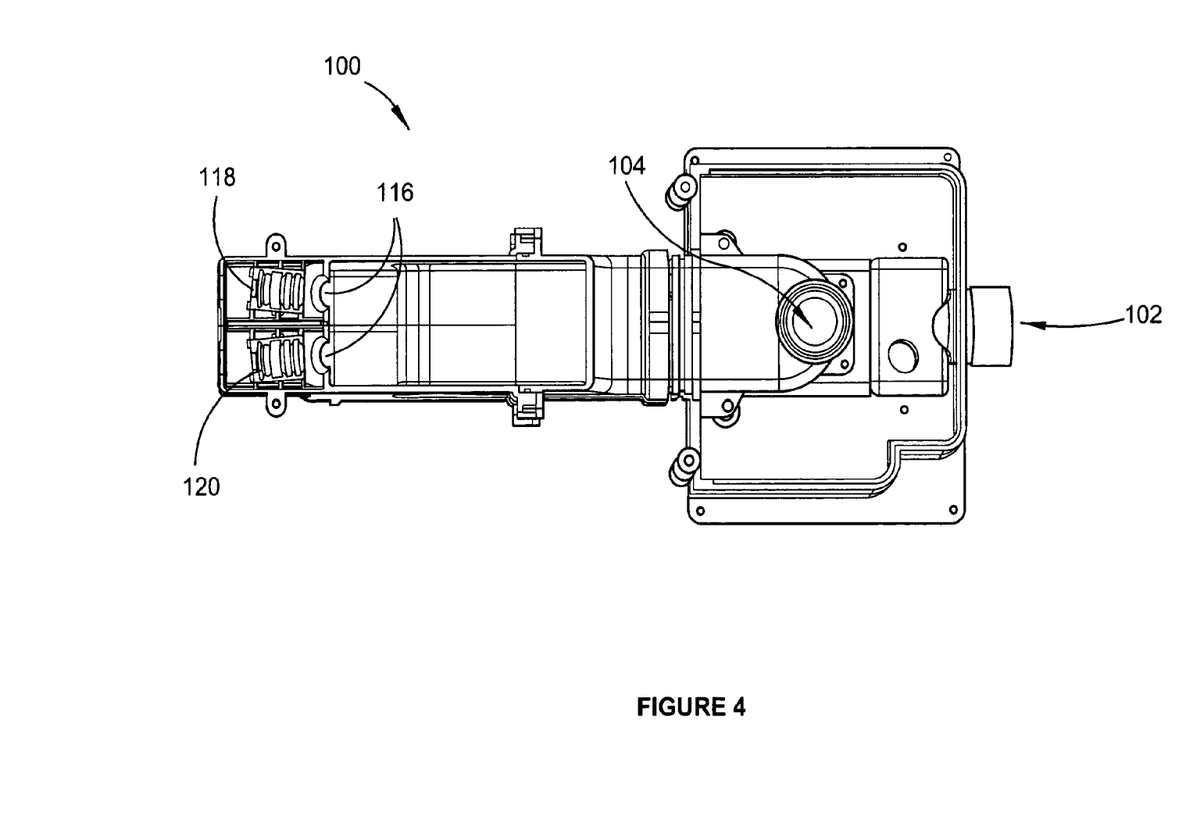
FIG. 4 shows a cross-sectional view through a top portion of the airflow-path of the detection chamber along line 3-3.

FIG. 2 illustrates a cross-sectional view through the detection chamber 100 along line 2-2 as illustrated in FIG. 1 and FIGS. 3 and 4 illustrate orthogonal cross sections through the lower and upper arms of the flow-path respectively.

Initially air is introduced into the inlet port 102. Next, the air traverses a flow sensor 106. In this embodiment, the flow sensor is an ultrasonic flow sensor operating in accordance with international patent publication WO/2004/102499 filed in the name of Vision Fire & Security Pty Ltd. The ultrasonic transducers 108 and 110 of the flow sensor are set on opposite sides of the centre line of the flow channel and are diagonally offset across the centre line of the flow-path. The cross section of the flow-path in the ultrasonic flow sensor 106 is generally rectangular. If desired the dimensions of the flow path at this point can be chosen to maintain the cross section of the flow-path within the flow sensor to be equal with the cross-sectional area of the input port 102. By matching these cross-sections no change in pressure is caused by the ultrasonic flow sensor, and moreover by choosing a relatively flat rectangular shape (or other elongate shape, e.g. an oval), the vertical extent of the ultrasonic flow sensor can be minimised. More particularly, it enables one of the dimension of the flow sensor perpendicular to the direction of travel of the ultrasonic signal to be kept low to prevent unwanted echoes (multipath effects) in the sensor. Next, the airflow passes along the lower part of the flow-path and flows around the bend 112 and enters a region of interest in the upper portion of the detection chamber.

FIG. 4 illustrates a cross-sectional view through the detection chamber 100 at this point. This portion of the detection chamber 100 includes several apertures e.g. 114 and 116 in its walls for enabling the light sources associated with the detection chamber to illuminate the airflow and also to enable a light receiver to receive scattered light from within the illuminated volume. In the cross-sectional views of FIGS. 2 and 4 an optical assembly 118,120 can be seen. These optical assemblies 118 and 120 include one or more light sources and associated optics for illuminating a volume within the detection chamber 100. The associated optics with each of the optical assemblies 118 and 120 can include one or more lenses and spatial apertures to define a desired illumination volume. For reasons which will become apparent the light source assemblies 118 and 120 are adapted to transmit light at an angle to the centre line of the detection chamber 100 and thus are angled with respect to the centre line.

Figure 5:
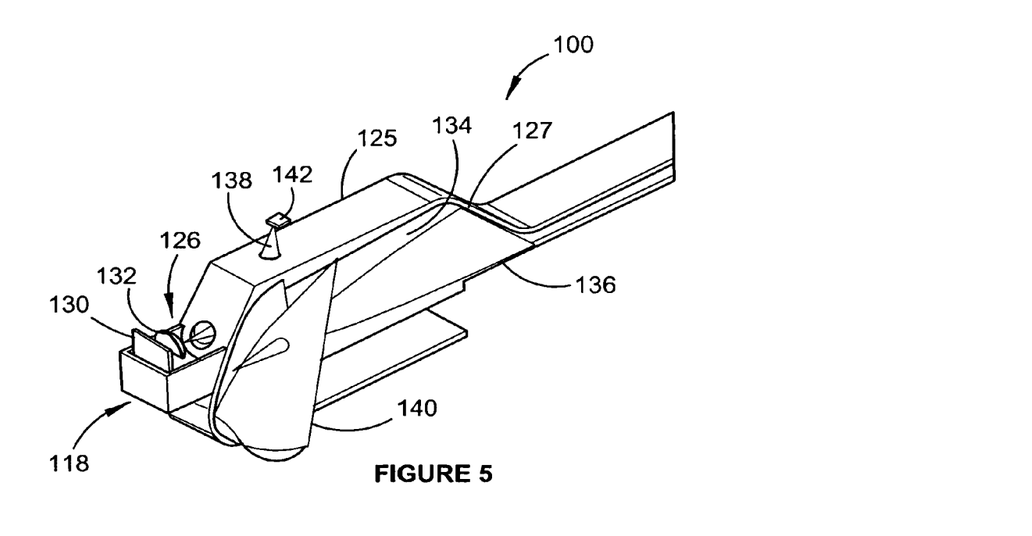
FIG. 5 illustrates a partial perspective view of part of the detection chamber, illustrating the volume illuminated by the light sources of the detector, and the field of view of the light receivers in an embodiment of the present invention.
Figure 6:
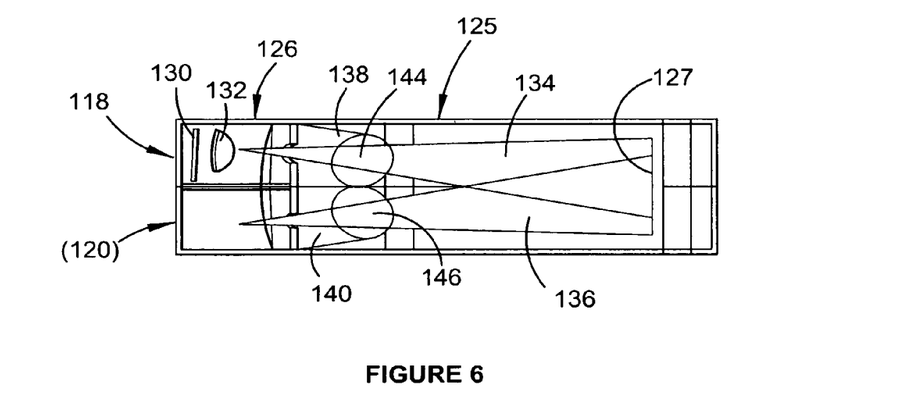
FIG. 6 illustrates a cross-section through the upper part of the detection chamber also illustrating the intersection between the field of view of the light receivers and the field of illumination of the light sources in an embodiment of the present invention.

This is better illustrated in FIGS. 5 and 6 which illustrate the illumination cones caused by each of the light sources and the fields of view of the light receivers. Turning first to FIG. 5, which illustrates a partial cutaway view of a portion of the detection chamber 100. In this view, part of the detection chamber housing 125 is illustrated. In a rearward portion of this housing 126 is mounted one of the optical assemblies 118 comprising a surface mounted LED on a circuit board 130. A lens 132 is also provided. The apertures through which the light shines defines a collimating iris to generate a first illuminated volume 134. A mirror image light source assembly which is not shown in this figure also generates a second illumination volume 136.

As can be seen in FIG. 6, because of the angular offset of the light sources with respect to the centreline of the flow-path the illuminated volumes 134 and 136 partially overlap, and do not intersect with the external walls of the chamber housing 125. The illumination volumes 134 and 136 are terminated by the angled back wall 127 of the housing 125. The wall 127 can be configured to include one or more baffles to control reflection from the surface 127.

The illumination volumes 134 and 136 intersect with the field of view 138 and 140 of correspondingly aligned light receivers, e.g. photodiode 142. The other photodiode is not shown in this figure. In this figure, the fields of view 138 and 140 are illustrated as cones to aid understanding. The intersection of the illuminated volume 134 and corresponding field of view 138 generate a corresponding region of interest 144, whereas the illumination volume 136 and corresponding light receiver field of view 140 form a second region of interest 146. In this embodiment the centre line of the field of view of the photodiodes is set at an angle of 67 degrees with respect to the centreline of the illuminated volume formed by its corresponding light source.

In use, when particles in the airflow passing through the detector 100 enter the field of view of one of the light receivers a portion of the light impinging on them in the illuminated volumes will be scattered into the field of view of the corresponding light receiver. The intensity of received light can be used to determine the concentration of particles in the airflow.

In the preferred embodiment of the present invention the light sources 118 and 120 emit radiation of different wavelengths. Most preferably, the light sources are capable of emitting at a large number of wavelengths. For example, the light source 120 may be adapted to emit light at a wavelength in the infrared whereas the other light source 118 may be adapted to emit light at a plurality of wavelengths, for example at three wavelengths, one in the blue, one in the green and one in the red portion of the electromagnetic spectrum. As will be appreciated by those skilled in the art other light emitting arrangements could be used, for example one or more broadband light sources could be used.

The light receivers 138 and 140 are preferably positioned with respect to their corresponding first and second light sources 134 and 136 such that the field of view of the first light receiver 138 and the volume illuminated by the second light source 136 do not intersect, and vice versa. However, as will be appreciated by those skilled in the art the volumes illuminated will not be clearly defined cones, as the light intensity from the light sources will drop off radially from the centre of the illuminated volume. The exact profile will depend on the light source used and optical configuration of the system. Therefore it should be understood that the preference for non-intersection of the field of view of the first light receiver and the second illuminated volume (and the second light receiver and the first illuminated volume) should not be understood to require no light from the light source to be within the field of view of the light receiver, but merely that the light level from the light source is below a certain acceptable threshold within the field of view of the receiver, for example the light level has fallen below the −3 dB point or to some other percentage of the peak intensity (e.g. 1%). Similarly the edge of the illuminated volume could be determined on the basis of the level of light energy.

The fields of view 138 and 140 of the two photodiodes are also arranged such that they substantially overlap at the surface of the detection chamber on which they impinge. This is done to enable the background subtraction algorithm to be implemented in the detector as described below.

Turning once again to the light sources 118 and 120, in a preferred form the light sources include an infrared LED 120 and a red, green, blue (RGB) LED 118. This enables four wavelengths of light in relatively compact physical space. Of course more or less wavelengths of light or electromagnetic radiation, inside or outside the visible range, could be used in other embodiments in the present invention.

In the preferred form the sample volume is illuminated sequentially at each of the four wavelengths. For example, the LED switching scheme can be implemented as listed in Table 1.

TABLE 1

Light-source switching and receiver status

| Time | Infrared | Red | Green | Blue | Detector status - IR photodiode | Detector status - RGB photodiode |
|---|---|---|---|---|---|---|
| 0 | On | Off | Off | Off | Primary | Secondary |
| 1.1 msec | Off | Off | Off | Off | Primary | Secondary |
| 2.2 msec | Off | On | Off | Off | Secondary | Primary |
| 3.3 msec | Off | Off | Off | Off | Secondary | Primary |
| 4.4 msec | Off | Off | On | Off | Secondary | Primary |
| 5.5 msec | Off | Off | Off | Off | Secondary | Primary |
| 6.6 msec | Off | Off | Off | On | Secondary | Primary |
| 7.7 msec | Off | Off | Off | Off | Secondary | Primary |

Figure 7:
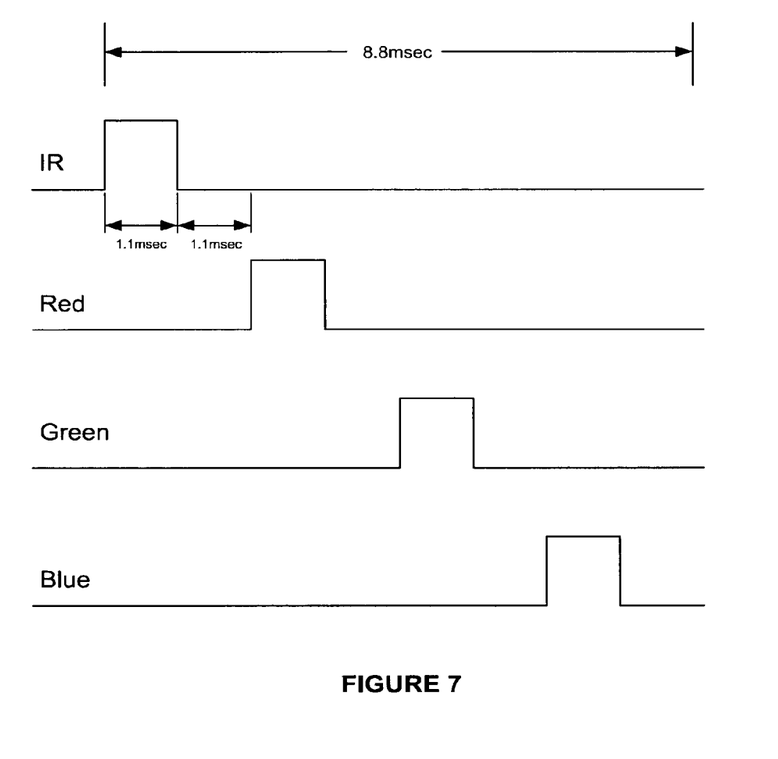
FIG. 7 illustrates a modulation scheme used in an embodiment of the present invention.

This cycle is repeated every 8.8 msec. A graphical representation of an 8.8 msec cycle of the driving waveform for the four wavelengths is illustrated in FIG. 7.

Figure 8:
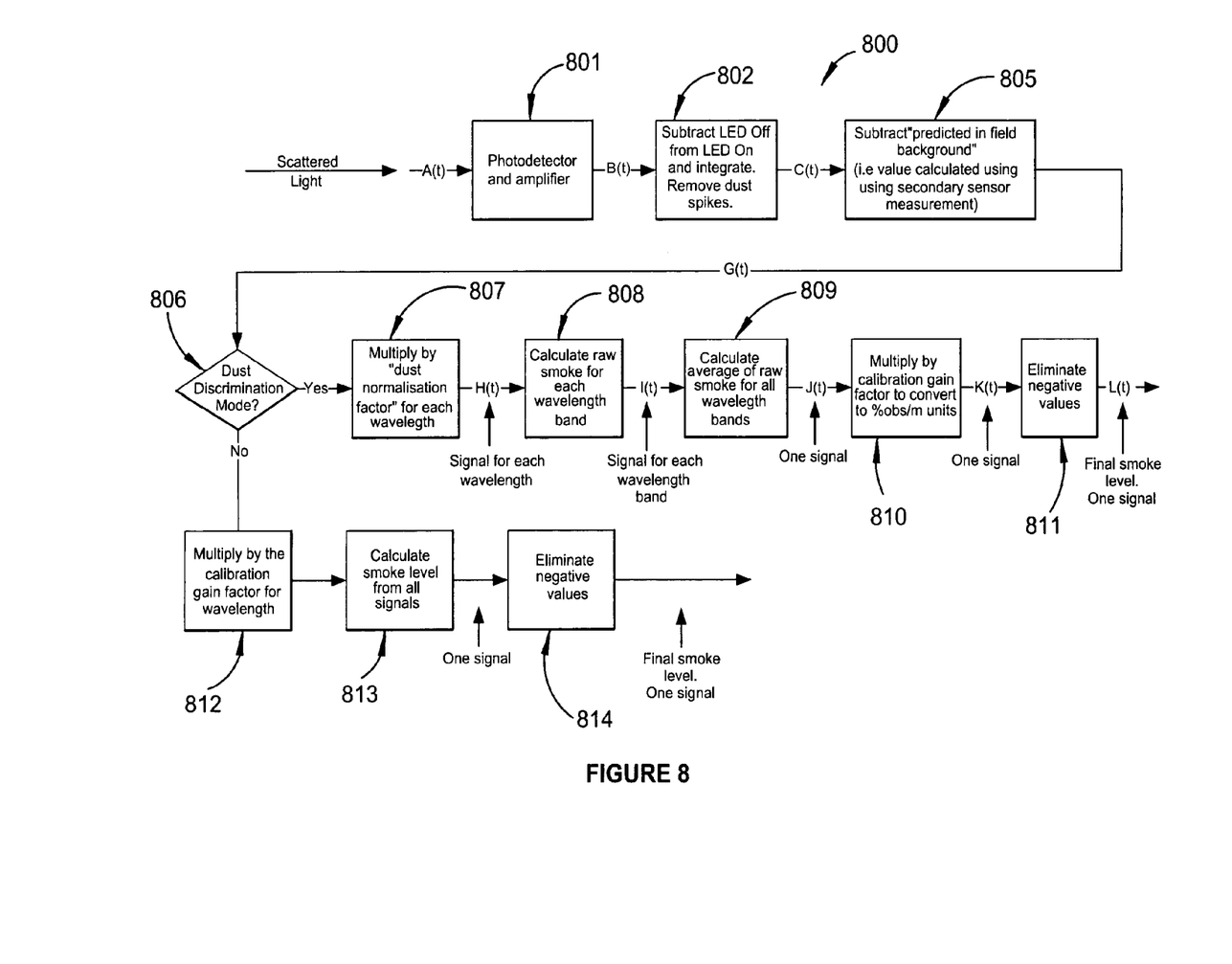
FIG. 8 illustrates a flowchart of the particle detection process used in an embodiment of the present invention.

In use four light scattering readings, one corresponding to each wavelength of light emitted by the pair of light sources 118 and 120 will be sequentially detected in accordance with the above modulation scheme. FIG. 8 shows a flowchart 800 of how the four light scattering readings are processed to generate a smoke detection level in accordance with an aspect of the present invention.

In the following discussion:

The signals B(t) through to H(t) each comprise IR, Red, Green, Blue components. For example C(t) has components $C_{IR}(t)$, $C_R(t)$, $C_G(t)$, $C_B(t)$, corresponding to the four wavelengths IR, Red, Green and Blue respectively.

Signal I(t) can comprises three signals, corresponding to wavelength bands e.g a band extending from Red to IR, or Blue to Green.

Signal L(t), K(t), J(t) are each single signals.

Initially the light sources are illuminated as indicated above and light is scattered by particles in the corresponding region of interest. The scattered light A(t) is sensed in step 801 by the corresponding primary photo-detector and then amplified. Either a high or low gain amplifier can be selected depending on the received light intensity.

Next in step 802 the amplified signal B(t) is digitised by an analog to digital converter. In one form of the invention, 8 readings at each wavelength are taken when the corresponding LED is turned on and then summed into an accumulated sum. Eight readings are also taken when the corresponding LED is turned off and then subtracted off the accumulated sum. In this step positive narrow spikes (i.e. transient high level signals) can also be removed as these spikes can be assumed to be due to dust particles passing through the region of interest. This sum is accumulated for 128 cycles (1126.4 msec) giving a raw smoke level at each wavelength C(t).

The background level is then subtracted in step 805 in the manner described below. The result is signal G(t).

Next at 806 if dust discrimination mode is configured steps 807 to 811 are performed. If dust discrimination is turned off then steps 812 to 814 are performed.

In the dust discrimination path, in step 807 the signal G(t) is multiplied by the measured dust normalisation factors NIR, NR, NG, NB (where NIR, NR, NG, NB are measured normalisation values which substantially equalise the values if the particle size is large i.e. in the case of dust). The result is signal H(t).

In step 808 the "raw smoke" levels are calculated for various wavelength bands in the manner described below.

In one case the raw smoke values are calculated as follows:

$$R \text{ to } IR \text{ band raw smoke} = (R_R - R_{IR})/(\lambda_R - \lambda_{IR}) \quad (1)$$

(where $\lambda_R$ is the wavelength of the red light)

$$G \text{ to } IR \text{ band raw smoke} = (R_G - R_{IR})/(\lambda_G - \lambda_{IR}) \quad (2)$$

$$B \text{ to } IR \text{ band raw smoke} = (R_B - R_{IR})/(\lambda_B - \lambda_{IR}) \quad (3)$$

Alternatively the raw smoke values could be calculated as follows:

$$B \text{ to } G \text{ band raw smoke} = (R_B - R_G)/(\lambda_B - \lambda_G) \quad (4)$$

$$G \text{ to } R \text{ band raw smoke} = (R_G - R_R)/(\lambda_G - \lambda_R) \quad (5)$$

$$R \text{ to } IR \text{ band raw smoke} = (R_R - R_{IR})/(\lambda_R - \lambda_{IR}) \quad (6)$$

These raw smoke values are the slopes of a graph of signal level H(t) versus wavelength. These signals are signal I(t) in FIG. 8.

The raw smoke signals in each band, e.g. "B to G raw smoke", "G to R raw smoke" etc. can be considered to be a measure of the concentration of particles in the particle size ranges most strongly scattered by the wavelengths, Blue to Green, Green to Red respectively. The raw smoke values in a band can be used to distinguish types of particles or smoke (or other characteristics of the particles or an event causing the emission of particles) e.g. if there are more particles in the size range measured by signal "B to G raw smoke" than there are in the range "G to R raw smoke" the conclusion may be made that the fire is in a flaming stage.

Figure 9A:
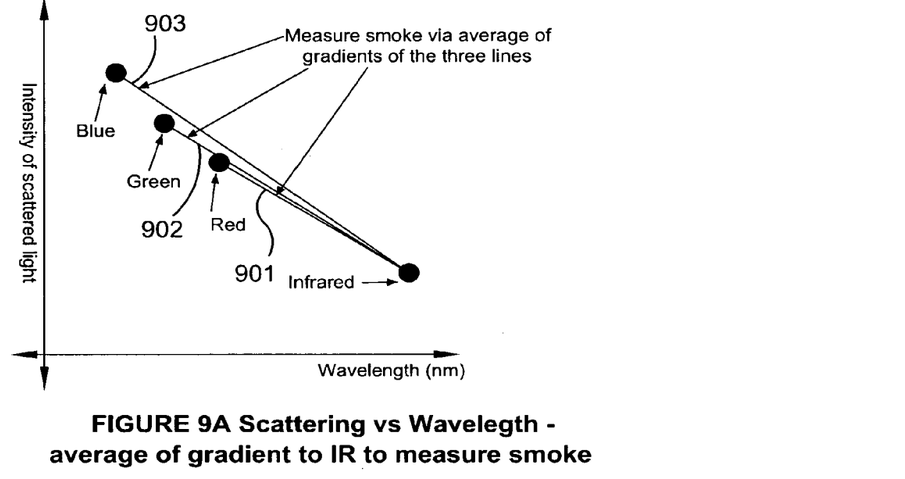
FIGS. 9A, 9B and 9C illustrate an exemplary output at four wavelengths using an embodiment of the present invention and three processing methods associated therewith.
Figure 9B:
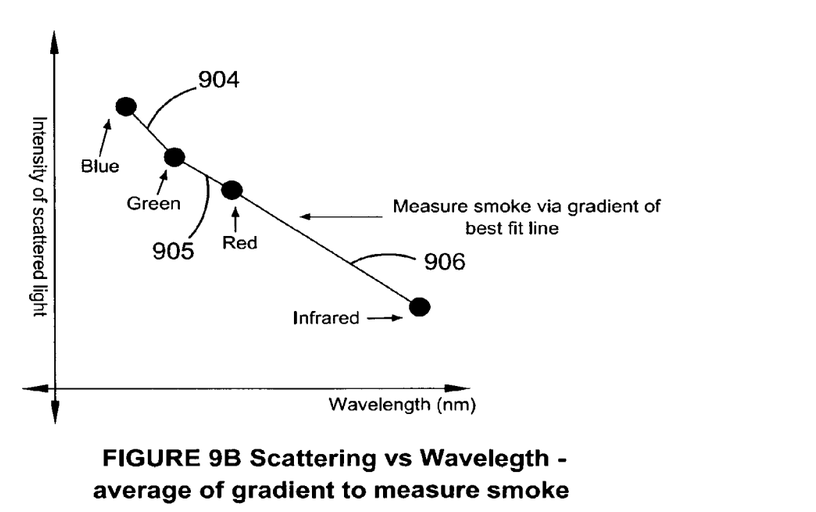

FIGS. 9A and 9B illustrate graphically the alternative processing schemes described in relation to step 808 of FIG. 8. In these figures a plot of H(t) at each of four wavelengths (blue, green, red, infrared) is illustrated.

In FIG. 9A the slope of the three lines 901, 902 and 903 are calculated using equations (1), (2) and (3) respectively.

In FIG. 9B the slope of the three lines 904, 905 and 906 are calculated using equations (4), (5) and (6) respectively.

Figure 9C:
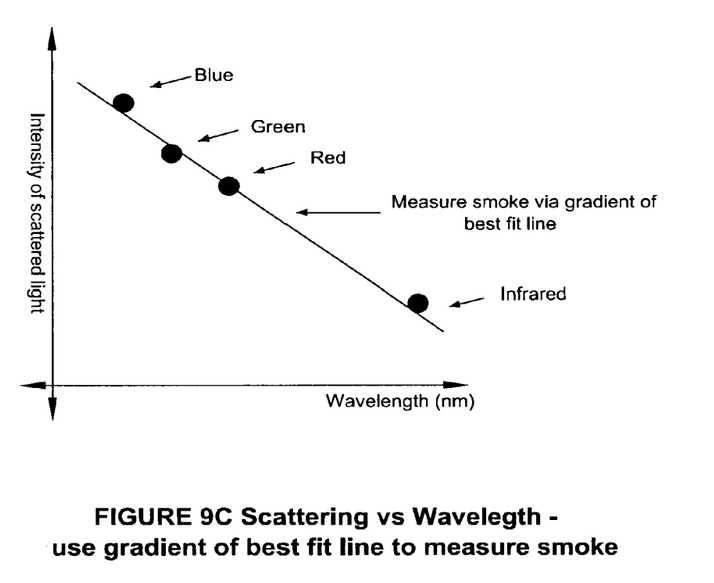

In each case, the three slope values are then combined to generate J(t) at 809 by taking the average of the three raw smoke signals. Alternatively, signal J(t) could be calculated as the gradient of the least squares error fitted line through a graph of the IR, Red, Green, blue components of signal H(t) v. wavelength as discussed below in relation to FIG. 9C. This version of the process essentially combines step 808 and 809 into a single step. FIG. 9C is a plot of H(t) at each of four wavelengths (blue, green, red, infrared). In the example illustrated in FIG. 9C, a line is fitted to the four intensity readings and the slope of the line is determined.

In other embodiments a different function may be fitted to the measurements. For example, a parabola or other function, and one or more parameters of that function can be used to determine the presence of smoke. For example, the gradient of a tangent to that curve could be determined and used to determine whether particles of interest or nuisance particles are the cause of the scattered light. In some implementations no fitting of a function will actually occur, however an equivalent mathematical operation can be implemented to form an approximation of the system behaviour as characterised by the ordered pair (x,y), where x is a signal indicative of the intensity of received light at a wavelength and y is a corresponding wavelength dependent parameter. In an alternative embodiment, the algorithm can apply a statistical method to the plurality of measurements. For example, a mean scattering level could be determined across the several wavelengths and a standard deviation from that mean determined.

In step 810 the signal J(t) is multiplied by a calibration gain factor to generate a smoke level in units of "% obscuration per meter". The result is signal K(t). Negative values of signal K(t) are removed at step 811. If K(t) is negative the result L(t) is set to zero. Otherwise L(t) is set equal to K(t). Preferably the signal L(t) is also limited to a maximum smoke level, say 32%/m.

At step 806, if dust rejection mode is not configured the smoke level is calculated as follows:

At step 812 the signal G(t) is multiplied by a calibration gain factor (preferably one gain factor for each wavelength). At step 813 the four values can be combined, e.g. added or averaged (with or without scaling), and any negative values removed in step 814 and a smoke level can be output.

The output smoke levels can then be further processed in any known manner according to alarm criteria to raise an alarm.

In the above computations it can be advantageous to normalise, either or both of:
the signals indicative of the intensity of received light at each of the wavelengths; and
their corresponding wavelength dependent parameters.

For example the raw smoke levels can be normalised to the smoke level at one of the wavelengths, or in one wavelength band. In one example the smoke values can be normalised to the smoke value at the longest wavelength. Similarly the wavelength dependent parameter can be normalised against one of the parameters, e.g. to the parameter corresponding to the longest wavelength.

As mentioned above in the preferred embodiment of the present invention the particle detection readings can be compared to a signature to characterise the particles in the chamber or the event producing the particles. This comparison with the signature can be performed at many different points in the process described above, e.g. any one of signals B(t) to (Lt) or a variation in these signals could be compared to a corresponding signature to characterise the particles in the chamber or the event producing the particles.

In a preferred form of the invention, the slope (at more one or more points) of one or more functions fitted to the particle detection readings is compared to known signatures.

In some cases it is advantageous to track a characteristic of detected particles over time. This time based data can be compared to a time based signature. Advantageously this allows certain events or conditions that have a particular temporal characteristic to be identified.

Signatures corresponding to various particle characteristics or events can be determined empirically.

In step 805 a background cancellation step is performed on the smoke readings E(t). This step is performed because over time, contamination of chamber walls will cause an increase in background light to be received by the photo-detectors.

Figure 10:
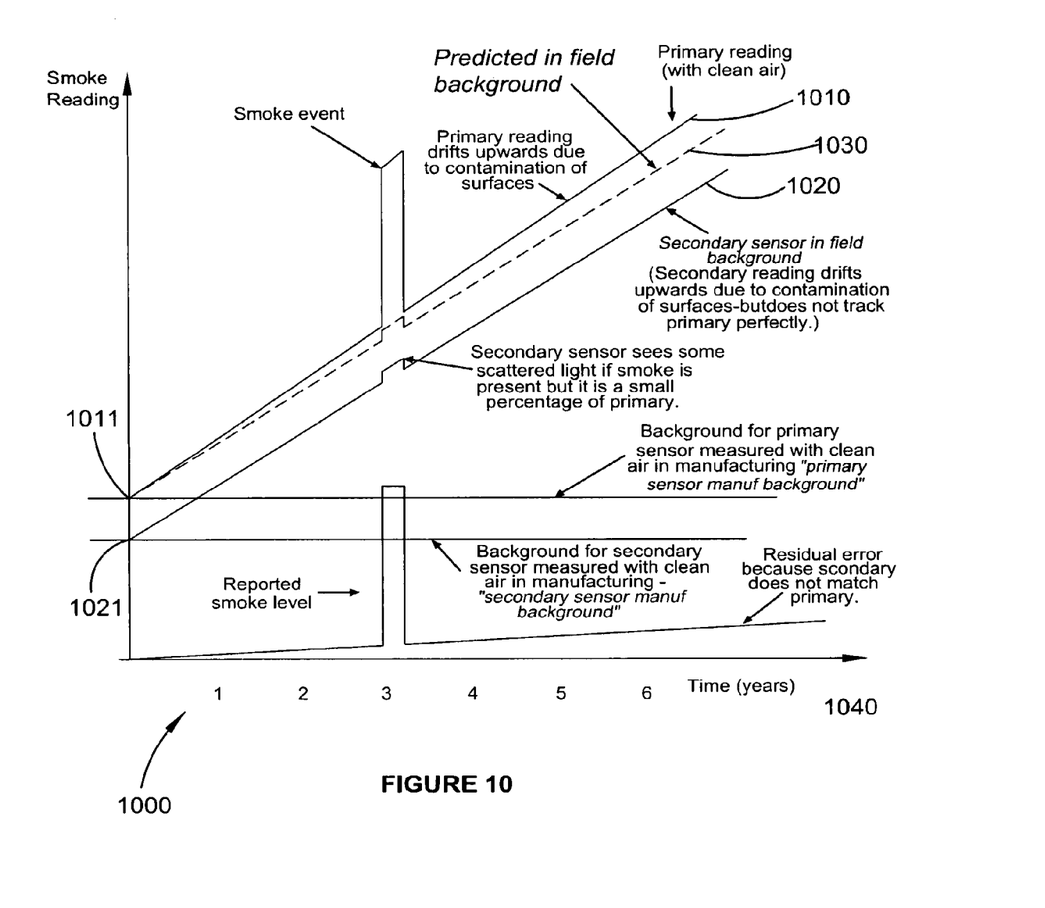
FIG. 10 is a graph illustrating the drift in a smoke detection system over time caused by soiling of the optical surfaces of the detection chamber.

FIG. 10 illustrates how this principle of background cancellation can be implemented in an embodiment of the present invention. Because of the physical structure of the chamber of the illustrated embodiment each light receiver can be used to provide a "background" light level reading for the other light receiver. To do this the geometry of the system is configured such that:

the fields of view of the two light receivers overlap at the wall of the chamber to the greatest extent possible—this ensures background light measured is comparable.

the field of view of each light receiver should not coincide with the field of illumination of the light source corresponding to the other detector—this ensures that light is not scattered directly from the beam associated with one detector into the other receiver.

In this manner each light receiver operates as a "primary detector", detecting primary light scattering when its associated light source is illuminated, and also operates as a "secondary detector" for detecting background light, when the light source associated with the other light source is illuminated. This concept is illustrated in Table 1 which indicates the photo-detector status corresponding to each illumination state in a system as illustrated in FIGS. 4 to 6, which includes 2 LEDs, one being an IR LED and the other a RGB LED.

Advantageously this allows the implementation of background cancellation for all measurements without including additional hardware.

Graph 1000 of FIG. 10 illustrates the long term light scattering reading, or smoke reading, from a detector, over several years. Plot 1010 illustrates the received scattered light level from a detector, before any compensation is applied, e.g. B(t). As can be seen plot 1010 increases steadily over time as contamination of the viewing and illuminated surface of the detection chamber occurs, increasing the background light level.

During manufacture it is possible to measure the background light level with the primary sensor in clean air to obtain "primary sensor manuf background" value 1011. The background level can also be measured with the secondary sensor in clean air to obtain "secondary sensor manuf background" 1021.

In use it is possible to periodically (e.g once per minute or hour) measure the secondary sensor value to determine a "secondary sensor in field background" value which is plotted as graph 1020. As can be seen plot 1020 also increases over time as contamination of the viewing and illuminated surface of the detection chamber occurs. Next it is possible to determine a predicted in-field background value as follows:

predicted in field background=primary sensor manuf background+(secondary sensor in field background−secondary sensor manuf background)

The value "predicted in field background" predicts the value the primary sensor would see in field if there was clean air in the chamber—this is illustrated by plot 1030.

Thus signal G(t) of FIG. 8 for a single colour is given by:

G(t)=B(t)Primary sensor−predicted in field background which is plotted as graph 1040 on FIG. 10.

It will be understood that the invention disclosed and defined in this specification extends to all alternative combinations of two or more of the individual features mentioned or evident from the text or drawings. All of these different combinations constitute various alternative aspects of the invention.

What is claimed is:

1. A particle detection system for including:
a detection chamber adapted to receive an air sample;
first particle detection means including a first light source for illuminating a first volume of the air sample at at least a first wavelength, and a first light receiver having a field of view intersecting with the first volume for receiving light scattered from the detection chamber and outputting a first signal indicative of the scattered received light;
second particle detection means including a second light source for illuminating a second volume of the air sample at at least a second wavelength, and a second light receiver having a field of view intersecting with the second volume for receiving light scattered from the detection chamber and outputting a second signal indicative of the scattered received light;
light source activation means adapted to selectively activate the first light source in a first time period and the second light source in a second time period; and
processing means adapted to receive a first signal from the first light receiver and a second signal from the second light receiver corresponding to the first time period and process the received signals to generate a first output corresponding to the first time period corrected for background light; and to receive a first signal from the first light receiver and a second signal from the second light receiver corresponding to the second time period and process the received signals to generate a second output corresponding to the second time period that is corrected for background light.

2. The particle detection system as claimed in claim 1 wherein the detection chamber includes at least one wall within the field of view of each of the first and second light receivers and wherein the first and second light receivers are positioned such that substantially the same portion of said chamber wall lies within the field of view of each of the first and second light receivers.

3. The particle detection system as claimed in claim 1 wherein the first and second light receivers are positioned with respect to their corresponding first and second light sources such that the field of view of the first light receiver and the second volume do not intersect, and the field of view of the second light receiver and the first volume do not intersect.

4. The particle detection system as claimed in claim 1 wherein the first and second wavelengths are different wavelengths.

5. The particle detection system as claimed in claim 1 wherein the first output corresponding to the first time period is corrected for background light by a process including subtracting the second signal indicative of the scattered received light corresponding to the first time period from the first signal indicative of the scattered received light corresponding to the first time period.

6. The particle detection system as claimed in claim 1 wherein the second output corresponding to the second time period is corrected for background light by a process including subtracting the first signal indicative of the scattered received light corresponding to the second time period from the second signal indicative of the scattered received light corresponding to the second time period.

7. The particle detection system as claimed in claim 1 wherein the first and second wavelengths are the same wavelengths.

* * * * *